United States Patent [19]
Heyse et al.

[11] Patent Number: 5,575,902
[45] Date of Patent: Nov. 19, 1996

[54] CRACKING PROCESSES

[75] Inventors: John V. Heyse, Crockett; Alan G. Kunze, El Cerrito; Steven E. Trumbull, San Leandro, all of Calif.

[73] Assignee: Chevron Chemical Company, San Ramon, Calif.

[21] Appl. No.: 269,764

[22] Filed: Jul. 1, 1994

Related U.S. Application Data

[63] Continuation-in-part of Ser. No. 177,822, Jan. 4, 1994.

[51] Int. Cl.$^6$ .................................................. C10G 9/16
[52] U.S. Cl. ........................ 208/48 R; 208/106; 208/47; 585/648
[58] Field of Search .................. 208/48 AA, 48 R, 208/47, 106; 585/648

[56] References Cited

U.S. PATENT DOCUMENTS

| | | |
|---|---|---|
| 1,883,630 | 10/1932 | Duff . |
| 2,063,596 | 12/1936 | Feiler . |
| 2,263,366 | 11/1941 | Peck et al. . |
| 2,818,374 | 12/1957 | Certa et al. . |
| 2,929,775 | 3/1960 | Aristoff et al. . |
| 3,160,671 | 12/1964 | Feigelman . |
| 3,169,000 | 7/1961 | Earnst et al. . |
| 3,178,321 | 4/1965 | Satterfield . |
| 3,284,526 | 11/1966 | Frayer . |
| 3,459,821 | 8/1969 | Engelbrecht . |
| 3,531,394 | 9/1970 | Kuszman . |
| 3,531,543 | 9/1970 | Clippinger et al. . |
| 3,536,776 | 10/1970 | Lo . |
| 3,584,060 | 6/1971 | Rausch . |
| 3,607,960 | 9/1971 | Button . |
| 3,617,359 | 11/1971 | Wakefield ................ 117/107.2 R |
| 3,631,215 | 12/1971 | Clippinger et al. . |
| 3,686,340 | 8/1972 | Patrick et al. . |
| 3,700,745 | 10/1972 | Kovach et al. . |
| 3,767,456 | 10/1973 | Glaski .................... 117/71 M |

(List continued on next page.)

FOREIGN PATENT DOCUMENTS

| | | |
|---|---|---|
| 0082920 | 7/1983 | European Pat. Off. . |
| 0146081 | 6/1985 | European Pat. Off. . |
| 0192059 | 8/1986 | European Pat. Off. . |
| 0351067 | 1/1990 | European Pat. Off. . |
| 1521848 | 4/1969 | Germany . |
| 317303 | 8/1929 | United Kingdom . |
| 313303 | 8/1929 | United Kingdom . |
| 1054121 | 1/1967 | United Kingdom . |
| 1122017 | 7/1968 | United Kingdom . |
| 1149163 | 4/1969 | United Kingdom . |
| 1604604 | 12/1981 | United Kingdom . |
| 2162082 | 1/1986 | United Kingdom . |
| 2234530 | 2/1991 | United Kingdom . |
| WO92/15653 | 9/1992 | WIPO . |
| WO94/15896 | 7/1994 | WIPO . |

OTHER PUBLICATIONS

Alon Processing, Inc.; "Alonized Steels for high temperature corrosion resistance"; 1990; pp. 1–19.
Berg et al., "Catalytic LPG Dehydrogenation Flts in '80s Outlook"; Oil and Gas Journal; pp. 191–197; Nov. 1980.
Dunn, "HP In Construction"; Hydrocarbon Processing; pp. 41–42; Aug. 1991.
General Motors, "The Carbon Gradient."
Gussow et al., "Dehydrogenation Links LPG to More Octanges"; Oil and Gas Journal; pp. 96–101; Dec. 1980.

(List continued on next page.)

*Primary Examiner*—Asok Pal
*Assistant Examiner*—Bekir L. Yildirim
*Attorney, Agent, or Firm*—Burns, Doane, Swecker & Mathis

[57] ABSTRACT

Methods for cracking hydrocarbons in reactor systems having improved resistances to carburization and coking. The reactor system comprises a steel portion having provided thereon a Group VIB metal protective layer to isolate the steel portion from hydrocarbons, applied to a thickness effective for completely isolating the steel portion from the hydrocarbon environment. The protective layer is anchored to the steel substrate through an intermediate carbide-rich, bonding layer.

1 Claim, 1 Drawing Sheet

U.S. PATENT DOCUMENTS

| | | | |
|---|---|---|---|
| 3,835,183 | 9/1974 | Carpenter et al. | |
| 3,864,284 | 2/1975 | Clippinger et al. | |
| 3,878,131 | 4/1975 | Hayes . | |
| 3,890,110 | 6/1975 | Glaski | 29/198 |
| 3,890,686 | 6/1975 | Caubet . | |
| 3,919,073 | 11/1975 | Bagnoli et al. | 208/47 |
| 3,955,935 | 5/1976 | Shockbey | 29/194 |
| 3,966,833 | 6/1976 | Cosyns et al. | |
| 4,013,487 | 3/1977 | Ramqvist et al. | |
| 4,015,950 | 4/1977 | Galland et al. | |
| 4,019,969 | 4/1977 | Golebiowski et al. | |
| 4,058,452 | 11/1977 | Loboda . | |
| 4,111,763 | 9/1978 | Pryor . | |
| 4,132,743 | 1/1979 | Caster et al. | |
| 4,161,510 | 7/1979 | Edridge . | |
| 4,163,706 | 8/1979 | Horowitz et al. | |
| 4,167,532 | 9/1979 | Walker et al. | |
| 4,167,533 | 9/1979 | Raymond . | |
| 4,173,457 | 11/1979 | Smith | 51/309 |
| 4,179,361 | 12/1979 | Michlmayr . | |
| 4,189,613 | 2/1980 | Bjornson . | |
| 4,191,632 | 3/1980 | Cosyns et al. | |
| 4,191,846 | 3/1980 | Farha, Jr. et al. | |
| 4,204,997 | 5/1980 | Hobbs et al. | |
| 4,208,302 | 6/1980 | McKay . | |
| 4,215,231 | 7/1980 | Raymond . | |
| 4,264,433 | 4/1981 | McKay . | |
| 4,268,188 | 5/1981 | Bertus et al. | |
| 4,271,008 | 6/1981 | Vogt et al. | |
| 4,297,150 | 10/1981 | Foster et al. | |
| 4,350,719 | 9/1982 | Baldi | 427/253 |
| 4,385,645 | 5/1983 | Campbell et al. | |
| 4,404,087 | 9/1983 | Reed et al. | |
| 4,410,418 | 10/1983 | Kukes et al. | |
| 4,438,288 | 3/1984 | Imai et al. | |
| 4,447,316 | 5/1984 | Buss . | |
| 4,451,687 | 5/1984 | Daly et al. | |
| 4,456,527 | 6/1984 | Buss et al. | |
| 4,463,206 | 7/1984 | Derrien et al. | |
| 4,467,016 | 8/1984 | Baldi . | |
| 4,471,151 | 9/1984 | Kolts . | |
| 4,488,578 | 12/1984 | Tseung et al. | |
| 4,507,196 | 3/1985 | Reed et al. | 208/48 AA |
| 4,511,405 | 4/1985 | Reed et al. | |
| 4,545,893 | 10/1985 | Porter et al. | |
| 4,551,227 | 11/1985 | Porter et al. | |
| 4,552,643 | 11/1985 | Porter et al. | |
| 4,555,326 | 11/1985 | Reid | 208/48 R |
| 4,595,673 | 6/1986 | Imai et al. | |
| 4,613,372 | 9/1986 | Porter et al. | |
| 4,665,267 | 5/1987 | Barri . | |
| 4,666,583 | 5/1987 | Porter et al. | |
| 4,685,427 | 8/1987 | Tassen et al. | |
| 4,686,201 | 8/1987 | Porter et al. | |
| 4,687,567 | 8/1987 | Porter et al. | |
| 4,692,234 | 9/1987 | Porter et al. | |
| 4,716,143 | 12/1987 | Imai . | |
| 4,727,216 | 2/1988 | Miller . | |
| 4,741,819 | 5/1988 | Robinson et al. | |
| 4,743,318 | 5/1988 | Fischer et al. | |
| 4,762,681 | 8/1988 | Tassen et al. | |
| 4,786,625 | 11/1988 | Imai et al. | |
| 4,795,732 | 7/1989 | Barri . | |
| 4,804,446 | 2/1989 | Lashmore et al. | 204/51 |
| 4,804,487 | 2/1989 | Reed et al. | |
| 4,827,072 | 5/1989 | Imai et al. | |
| 4,863,892 | 9/1989 | Porter et al. | 502/170 |
| 4,902,849 | 2/1990 | McKay et al. | |
| 4,917,969 | 4/1990 | Pircher et al. | |
| 4,925,549 | 5/1990 | Robinson et al. | |
| 4,926,005 | 5/1990 | Olbrich et al. | |
| 4,976,932 | 12/1990 | Maeda et al. | |
| 4,982,047 | 1/1991 | Barri et al. | |
| 5,012,027 | 4/1991 | Abrevaya et al. | |
| 5,015,358 | 5/1991 | Reed . | |
| 5,053,574 | 10/1991 | Tsutsui et al. | |
| 5,118,028 | 6/1992 | Ogawa et al. | |
| 5,139,814 | 8/1992 | Sugaro . | |
| 5,139,914 | 8/1992 | Tomiyama et al. | |
| 5,238,492 | 8/1993 | Itoh et al. | 106/436 |
| 5,242,665 | 9/1993 | Maeda et al. | |
| 5,298,091 | 3/1994 | Edwards, III et al. | 148/232 |

OTHER PUBLICATIONS

W. A. McGill and M. J. Weinbaum, "The Selection, Application and Fabrication of Alonized Systems in the Refinery Environment"; 1975; pp. 1–18.

Micron, Inc., Analytical Service Laboratory; "Report #R–8126, Alonized Steel"; Jun. 1985.

Pujado et al., "Make $C_3$–$C_4$ Olefins Selectively"; Hydrocarbon Processing; pp. 65–70; Mar. 1990.

Pujado et al., "Production of LPG Olefins by Catalytic Dehydrogenation"; Energy Progress; vol. 4, No. 3; pp. 186–191; Sep. 1984.

Pujado et al., "OGJ Report"; Oil and Gas Journal; pp. 71–74; Mar. 1983.

Shinohara, Kohchi, Shibata, Sugitani and Tsuchida; "Development of nondestructive technique for measuring carburization thickness and a new carburization–resistant alloy"; Werkstoffe und Korrosion, 1986; pp. 410–411.

Toyo Engineering Corp. and Kubota; "CORET, New Cracking Tube to Retard Coke Depositions"; Mar. 1986; pp. 1–5.

Toyo Engineering Corp. and Kubota: "Development of Double–Layer Cast Tube for Anti–Carburization and the Retarding of Coke Deposition"; pp. 1–11.

King et al., "The Production of Ethylene by the Decomposition of n–Butane; the Prevention of Carbon Formation by the Use of Chromium Plating", Transactions of the E.I.C., vol. 3, No. 1, p. 1, (1959).

Platt's International Petrochemical Report (Oct. 1993).

J. R. Bernard, "Hydrocarbons Aromatization on Platinum Alkaline Zeolites", Proceedings of the Fifth Int. Conf. Zeolites, pp. 686–695, Heydon, London (1980).

FIGURE
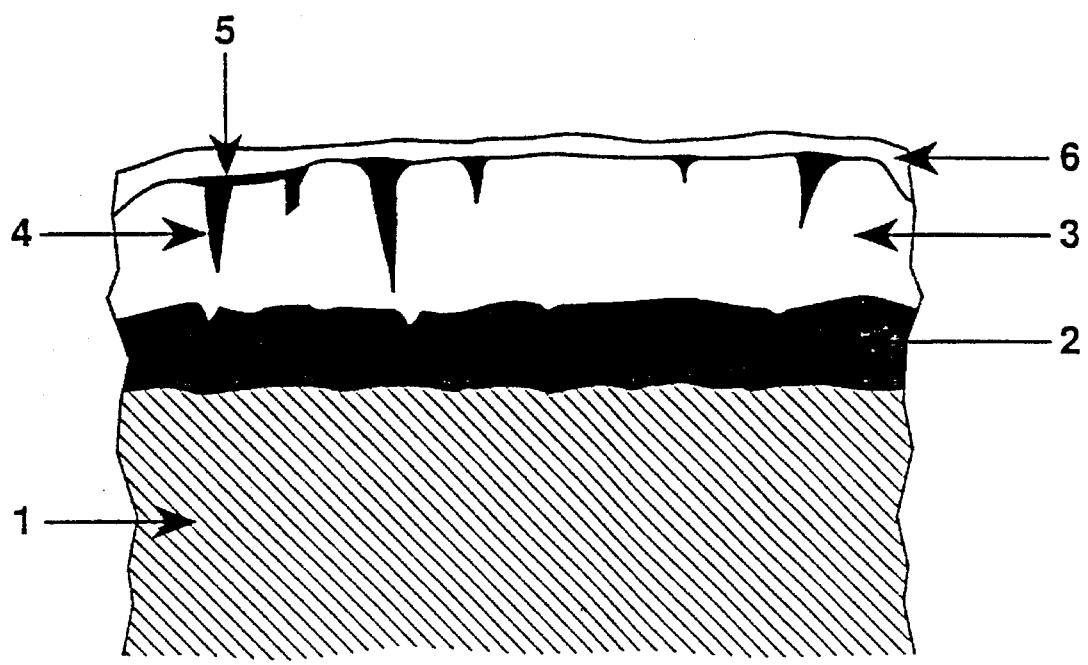

CRACKING PROCESSES

BACKGROUND OF THE INVENTION

This application is a continuation-in-part of application Ser. No. 08/177,822, filed Jan. 4, 1994, the contents of which are hereby incorporated by reference.

The invention relates to processes for the cracking of hydrocarbons, particularly for the thermal cracking of a gaseous stream containing hydrocarbons.

In thermal cracking operations a diluent fluid such as steam is usually combined with a hydrocarbon feed such as ethane and/or propane and/or naphtha, and introduced into a cracking furnace. Within the furnace, the feed stream which has been combined with the diluent fluid is converted to a gaseous mixture which primarily contains hydrogen, methane, ethylene, propylene, butadiene, and small amounts of heavier gases. At the furnace exit this mixture is cooled to remove most of the heavier gases, and then compressed. The compressed mixture is routed through various distillation columns where the individual components such as ethylene are purified and separated.

One recognized problem in thermal cracking is the formation of coke. Because coke is a poor thermal conductor, as coke is deposited higher furnace temperatures are required to maintain the gas temperature in the cracking zone at necessary levels. Higher temperatures increase feed consumption and shorten tube life. Also, cracking operations are typically shut down periodically to burn off deposits of coke. This downtime adversely affects production.

Another problem in thermal cracking is the embrittlement of the steel walls in the reaction system. Such embrittlement is due to carburization of the system metallurgy, and ultimately leads to metallurgical failure.

A variety of solutions have been proposed for addressing the problem of coke formation in thermal cracking processes. U.S. Pat. No. 5,015,358 describes certain titanium antifoulants; U.S. Pat. Nos. 4,863,892 and 4,507,196 describe certain antimony and aluminum antifoulants; U.S. Pat. Nos. 4,686,201 and 4,545,893 describe certain antifoulants which are combinations of tin and aluminum, aluminum and antimony, and tin, antimony and aluminum; U.S. Pat. Nos. 4,613,372 and 4,5524,643 describe certain antifoulants which are combinations of tin and copper, antimony and copper, and tin, antimony and copper; U.S. Pat. Nos. 4,666,583 and 4,804,487 describe certain antifoulants which are combinations of gallium and tin, and gallium and antimony; U.S. Pat. No. 4,687,567 describes certain antifoulants which are combinations of indium and tin, and indium and antimony; U.S. Pat. No. 4,692,234 describes certain antifoulants which are combinations of tin and silicon, antimony and silicon, and tin, antimony and silicon; U.S. Pat. No. 4,551,227 describes certain antifoulants which are combinations of tin and phosphorus, phosphorus and antimony, and tin, antimony and phosphorus; U.S. Pat. No. 4,511,405 describes certain tin antifoulants, and antifoulants which are combinations of tin and antimony, germanium and antimony, tin and germanium, and tin, antimony and germanium; U.S. Pat. No. 4,404,087 describes certain tin antifoulants, and antifoulants which are combinations of tin and antimony, germanium and antimony, tin and germanium, and tin., antimony and germanium; and U.S. Pat. No. 4,507,196 describes certain chromium antifoulants, and antifoulants which are combinations of chromium and tin, antimony and chromium, and tin, antimony and chromium.

In King et al, "The Production of Ethylene by the Decomposition of n-Butane; the Prevention of Carbon Formation by the Use of Chromium Plating", Trans. of the E.I.C., 3, #1, 1 (1959), there is described an application of a 3/1000 inch thick chromium plate to a stainless steel reactor. This chromium plate is described as peeling-off the surfaces of the steel after a period of several months of operation, which was attributed to the high temperatures required for the reaction, and periodic heating and cooling.

SUMMARY OF THE INVENTION

Accordingly, one object of the invention is to provide an improved method for the cracking of hydrocarbons, where catalytic coking is minimized, and carburization in the reactor system is reduced.

Among other factors the invention is based on the discovery that a chromium protective layer effective for resisting carburization and coking, can be provided on a portion, or portions of the reactor system exposed to hydrocarbons, which, unlike prior art chromium layers, is resistant to peeling.

According to this invention an intermediate bonding layer is used which anchors the chromium protective layer to the steel substrate to be protected. In this regard, the reactor system comprises a steel portion having provided thereon a chromium protective layer to isolate the steel portion from hydrocarbons, applied to a thickness effective for completely isolating the steel portion from the hydrocarbon environment. The protective layer is anchored to the steel substrate through an intermediate carbide-rich, bonding layer.

Cracks have been observed to form in chromium protective layers, especially after the initial heating of an electroplated material. These cracks can allow steam (which is typically present) to attack the steel/chromium interface and undermine the chromium protective layer. According to another embodiment of the invention there is provided a novel procedure which includes a step of treating a chromium coated surface with hydrocarbons in the absence of steam which produces a metal carbide filler of the cracks which effectively seals-off the chromium coating and carbide-rich bonding layer from $H_2O$ attack.

In yet another embodiment of the invention, a protective layer is formed by bonding a chromium layer to steel in the presence of a nitrogen-containing compound at elevated temperature. This has the advantage of forming not only a carbide-rich bonding layer, but also results in the filling of cracks in the chromium layer with chromium nitride which effectively seals off the carbide-rich bonding layer from $H_2O$ attack.

An effective protective layer must resist deleterious chemical alteration, as well as peeling. Additionally, the protective layer must maintain its integrity through operation. As such, the protective coating must be sufficiently abrasion resistant during start-up and operation. The chromium-based coatings according to the invention have these advantages.

Preferably, the chromium protective layer is applied as a reducible paint which upon curing in a $H_2$-rich (or pure) environment, in the absence of hydrocarbon or steam, forms a continuous chromium metal layer of substantial thickness, indistinguishable from an electroplated material, except that it is virtually free of cracks and very finely and cleanly anchored to the underlying steel through a carbide-rich bonding layer. Chromium paint protection can be applied and cured in situ to an existing plant.

Moreover, a chromium paint such as that described above can be applied to a previously chromium-plated surface. The curing treatment for the paint causes chromium metal to fill cracks in the plate as they form, thereby producing a smooth, substantially crack-free chromium coating. The paint can also be used to repair damaged, previously chromium-plated steel.

The chromium paints are especially useful to treat welds and other hard to reach areas that are otherwise untreatable by plating.

With the foregoing, as well as other objects, advantages, features and aspects of the disclosure that will become hereinafter apparent, the nature of the disclosure may be more clearly understood by reference to the detailed description and the appended claims.

BRIEF DESCRIPTION OF THE DRAWING

The drawing schematically illustrates the various metallic layers that are produced on a base construction material (e.g., HK-50) after the steel has been plated with chromium, heat treated in nitrogen at 1800° F. for 2 hours (nitrogen curing) and then subjected to steam at 1800° F. FIG. 1 shows that overlaying and incorporating part of the steel surface is a bonding layer (glue layer) of chromium that is rich in chromium carbides. A thicker layer of metallic chromium overlays this bonding layer. The chromium layer contains cracks produced during the plating process, some of which formed as the plate cooled. These cracks have been filled in with chromium nitride, which was formed during the nitrogen cure step. At the outer surface is a thin layer of chromium oxide.

DETAILED DESCRIPTION OF THE PREFERRED EMBODIMENTS

The invention will be described hereinafter in terms of the thermal cracking of a hydrocarbon feed to produce e.g., ethylene. However, the various aspects of the invention are not intended to be limited to that embodiment. As will be apparent to those skilled in the art, they are useful in other areas of high temperature hydrocarbon processing such as both thermal and catalytic cracking of a variety of feeds to produce a variety of desired products. Also, while the invention is described in terms of using chromium to produce a protective layer, molybdenum, tungsten, and mixtures thereof, with or without the use of chromium, may be used as well.

While the invention will be presented generally as a process for improved cracking of hydrocarbons, there are also other aspects of the invention. Thus, the invention relates to a method of protecting a steel portion of a reactor system that is to be contacted with hydrocarbons at elevated temperatures, and to a process for preparing a substantially crack-free Group VIB metal (i.e., chromium, molybdenum or tungsten) protective surface on a steel portion of a reactor system that is to be contacted with hydrocarbons at elevated temperatures. Moreover, the invention is directed to certain Group VIB metal paints for application to a steel system for contacting hydrocarbons at elevated temperatures, and to a steel portion of a reactor system having a Group VIB metal protective layer.

Generally the invention is directed to a process for thermally cracking hydrocarbons. The process comprises (i) providing a carburization, abrasion and peeling resistant chromium protective layer to a steel portion of a cracking reactor system by (a) applying to the steel portion a chromium plating, cladding or other coating of chromium effective for forming a carburization resistant protective layer, to a thickness effective to isolate the steel portion from hydrocarbons during operation, and (b) forming the protective layer, anchored to the steel portion through an intermediate carbide-rich bonding layer; and then, (ii) thermally cracking a hydrocarbon feed. Preferably said thermal cracking is carried out in the presence of steam, as is well known in the art.

"Reactor system" as used herein refers to a reactor for contacting with hydrocarbons at elevated temperatures, as well as associated heat exchangers, piping, etc. Preferably, the reactor system is at least one cracking furnace, including any cracking or furnace tubes thereof, effective to crack a feed material into desired products such as ethylene.

By "surfaces susceptible to carburization," there is intended at least those surfaces of the reactor system that are in contact with hydrocarbons during processing wherein carburization will take place under reaction conditions. Typically those surfaces susceptible to carburization to which protective layers according to the invention should be applied are those portions of the reactor system which exhibit skin temperatures of at least 1200° F., preferably at least 1500° F., and most preferably at least 1700° F., during operation. The higher the temperature, the more important it is to apply a protective layer.

The chromium protective layer according to the invention can be applied as a plating, cladding or other coating such as chromium-containing paint or by chemical vapor deposition. Then the plating, cladding or other coating is treated in a manner effective to form a protective layer which is anchored to the steel substrate through a carbide-rich bonding layer thereby providing the necessary abrasion resistance, and resistance to peeling. Preferably, the plating, cladding, or coating is resistant to abrasion, peeling or flaking for a period of 1 year, preferably 2 years, and more preferably 3 years such that the reactor system will maintain its carburization resistant properties without reapplication.

Another method of applying a metallic coating or cladding to steel is known as sputtering. For example, see U.S. Pat. No. 5,298,137 to Marshall, which describes a method and apparatus for DC linear magnetron sputtering. This and other sputtering techniques, which produce thick and even coatings of metals, can be used to apply Cr, W, or Mo coatings to, for example, the inner surfaces of cracker furnace tubes.

It is important that the chromium be applied so that it does not readily peel off. Some methods of applying chromium, for example, methods for applying so-called "decorative chrome" plating are not suitable. These methods utilize an underlying copper or nickel layer, which can interfere with formation of the desired chromium/steel bonding layer.

Forming a protective layer suitably anchored to the steel substrate and resistant to carburization, will depend on treatment after application of the chromium. Once applied, the chromium plating, cladding or other coating should be cured at a temperature, and for a time effective to produce the intermediate carbide-rich bonding layer. For example, curing can be done at 1700° to 1850° F. for 2 to 4 hours.

It is also helpful to prepare the steel surface before application of the chromium (or other Group VIB metal) so that the steel surface is clean of metal oxides (e.g., rust, chromium oxide), dirt, dust, etc., e.g. by honing or scraping the steel surface. Some surface pretreatment procedures are discussed in the Metals Handbook, Ninth Ed., Vol. 5, page 172. Furthermore, prior to applying the Group VIB metal, it is preferred to stress relieve hard steels (hardness exceeding 40 HRC) by heating to 150°–230° C.

Where practical, it is preferred that the resistant materials be applied in a paint-like formulation (hereinafter "paint") to a new or existing reactor system. Such a paint can be sprayed, brushed, pigged, etc. on reactor system surfaces such as mild steels or stainless steels, and will have viscosity characteristics sufficient to provide a substantially continuous coating of measurable and substantially controllable thickness.

Chromium-containing paints are particularly preferred as they are less expensive than chromium plating, and will produce a protective layer exhibiting fewer cracks. In fact, protective layers formed from chromium-containing paints have been observed to be relatively crack-free. Additionally, paints can be used to provide protective layers to areas not readily accessible to e.g., platings, such as welds. In this regard, combinations of techniques can be used. For example, platings can be used for easily accessible areas while paints can be used for those areas not readily accessible to platings. Also, a chromium-containing paint can be applied to a newly or previously chromium plated surface to fill cracks.

The thickness of the paint after application should be between 0.1 and 15 mils, preferably 1 and 10 mils, and more preferably between 2 and 8 mils. The metallic coatings and, in particular, the paints, are then preferably treated under reducing conditions with hydrogen. Curing is preferably done in the absence of hydrocarbons. It is important to avoid formation of metal oxides under the carbide-rich bonding layer, so curing is preferably done in the absence of oxygen and steam. Curing results, for example, in a strong protective layer preferably between 0.5 and 10 mils thick, and more preferably between 1 and 4 mils thick.

Analysis by petrographic microscopy of a cross-section of the caoted steel can readily determine the thickness of the protective layer. For ease of measurement of paint and coating thickness, coupons can be prepared which correspond to the painted reactor surface. These can be treated under identical conditions to the reactor system treatment. The coupons can be used to determine paint and coating thickness.

In addition to applied thickness, viscosity and other properties of the paint are important. The viscosity should be such that the paint can be easily applied and that it does not drip or pool due to gravity.

Preferred paints comprise Group VIB salts that melt below 2000° F., preferably below 1800° F., and more preferably below 1600° F. The group VIB metals are chromium, tungsten and molybdenum. Preferably these salts are reducible, for example with hydrogen, and thereby produce a continuous phase that is not subject to coking or carburization.

A preferred paint according to the invention comprises a Group VIB metal halide (which is a solid), a binding agent (binder), and optionally a solvent to thin the binder or to thin the mixture. Paint binding agents are well known in the art. They are used to help suspend solids to produce flowable and spreadable paints. A preferred binding agent for use in this invention is a metal salt, such as an organometallic compound, that is a liquid at about room temperature. It preferably has a viscosity higher than or similar to paint. Examples of such salts are Group VIB metal salts of organic acids, such as chromium hexanoate, chromium octanoate, chromium ethylhexanoate and chromium decanoate. Other metal salts can also be used as a binder—for example, zirconium hexanoate—so long as the binder does not interfere with the formation of the protective layer or formation of a continuous bonding layer. Additionally, the binder or products produced from the binder must not induce coke formation.

Optionally, finely ground metal powder can be added to the paint, for example, chromium powder having a particle size of 1–5 microns.

The invention also includes paint formulations comprising each of the other Group VIB metals, as well as for paints containing more than one Group VIB metal.

The use of paints containing chromium halides is preferred, especially chromium chlorides ($CrCl_2$ and $CrCl_3$). Paints based on chromium halides appear to be self-fluxing and form strongly adherent coatings. One advantage of the chromium coatings is that they do not result in liquid metal embrittlement. Chromium paints are preferably reduced at high temperatures in order to produce metallic chromium-containing coatings. Useful reduction temperatures are above 1200° F., preferably at about 1400° F. or higher (e.g., 1500° F.).

One preferred paint according to the invention comprises the following components: 1) a chromium halide, 2) a binder comprising a liquid organochromium compound, and 3) a solvent. By solvent is meant a single organic compound or a mixture of organic compounds that at least partially dissolves the binder. The solvent preferably is evaporated before curing.

Another preferred paint according to the invention comprises the following components: 1) chromium ethylhexanoate; 2) chromium chloride ($CrCl_3$); 3) chromium metal powder (1–5 micron); and 4) solvent. Chromium ethylhexanoate is advantageous in that it acts as a binder by holding the other components in suspension, it dries to form a solid surface, and it decomposes at about 500° F. Chromium chloride acts as a flux to clean the steel surface, and decomposes to give chromium suitable for attachment to steel. Chromium metal powder acts as an additional supply of chromium, and helps to maintain the suspension. The solvent is chosen such that the formulation is paintable. Furthermore, the addition of solvent reduces the proportion of chromium ethylhexanoate, which is slow drying.

One formulation for the above paint is to mix a 1:1:1 ratio (by weight) of chromium ethylhexanoate, chromium chloride, and chromium powder, plus sufficient solvent to provide a paintable coating. The paint can then be treated as described above to provide a chromium protective layer. For example, the paint can be treated at 1400° F. in a reducing environment of at least 50% $H_2$, with the remainder in $N_2$, for up to 48 hours.

A paint can also be used in which tungsten and/or molybdenum powders are partially or wholly substituted for chromium powder.

It is important to prevent generation of chromium oxide during formation of the protective metal layer. Therefore, it is generally preferable not to include metal oxides in the paint. However, a molybdenum oxide paint is possible since that oxide melts below 1500° F., and can be reduced in-situ with hydrogen.

Another example of a useful paint would be one comprising a fusible $CrCl_2$ or $CrCl_3$ salt which may or may not be incorporated with solvents and other additives. Other specific formulations include finely ground $CrCl_3$ in 90 wt. gear oil to form a viscous liquid, and finely ground $CrCl_3$ in a petroleum jelly carrier. Such a paint provides a simple low cost method of applying chromium to steel, as it provides clean contact with the steel substrate which permits curing procedures to firmly attach the chromium to the steel. As an example, the paint can be reduced in $H_2$ or another suitable gas at about 1500° F. for 1 hour.

Thicker protective layers can also be provided. For example, layers can be built-up by successively painting and curing the steel surface.

While a variety of materials such as tin, antimony, germanium, etc. have been suggested for use as antifoulants in thermal cracking processes, chromium-based protective layers would likely be more desirable under cracking conditions than one which is tin-based, for example. A chromium protective layer has exhibited good resistance to a number of environments such as carburizing, oxidizing, and chloriding environments. Chromium is believed to be more robust than tin under such conditions. In this regard, tests suggest that a chromium plating is more resistant to metal migration (loss), and a chromium coating would be harder making it less likely to rub off.

As an example of a suitable paint cure, the system including painted portions can be pressurized with $N_2$, followed by the addition of $H_2$ to a concentration greater than or equal to 50% $H_2$. The reactor inlet temperature can be raised to 500° F. at a rate of 10°–100° F./hr. Thereafter the temperature can be raised to a level of 1400° to 1600° F. at a rate of 10°–20° F./hr, and held within that range for about 48 hours. Curing can also be achieved in pure $H_2$ at 1300° F. to 1600° F. for 2–24 hours to develop the carbide-rich bonding layer.

For chromium-containing paints, it is preferable to initially cure the paint at temperatures typically exhibited during thermal cracking. Curing temperatures between 1200° and 1800° F., preferably between 1400° and 1800° F., provide a carburization-resistant chromium protective layer anchored to a steel substrate through a carbide-rich bonding layer.

Slow heating can minimize crack formation. Inevitably, however, cracks will appear in the chromium layer due to different thermal expansion properties of the base steel and the chromium. Therefore, in a preferred embodiment the cured plating, cladding, or other coating is then contacted with hydrocarbons at temperatures common to a cracking environment (e.g., about 1750° to 2050° F.), with steam addition rates reduced or minimized, or more preferably, in the absence of steam. The hydrocarbons used in this treatment step should be relatively free of impurities, preferably completely free of impurities, such as oxygen compounds, sulfur compounds, and water. Useful hydrocarbons include ethane, propane, butane, and the like. This treatment will form chromium carbides which over time (e.g. 0.5 to preferably 24 hours) will fill the cracks and effectively seal the chromium coating and carbide-rich bonding layer from later $H_2O$/steam attack during cracking.

The cured chromium carbide surface is preferably treated with steam prior to being subjected to cracking service. This steam treatment, in the absence of hydrocarbons, produces a thin chromium oxide layer over the exposed chromium carbide layer. This oxide layer protects the chromium carbides from attack by metal antifoulant compounds and feed impurities, such as sulfur compounds.

Thus, in a further preferred embodiment, the cured and hydrocarbontreated plating, cladding or other coating can be then treated with steam at a temperature (e.g. $\geq$ 1700° F.), and for a time effective to produce an oxide coating on the surface to be contacted with the hydrocarbons during cracking. It has been surprisingly found that at lower temperatures steam will penetrate and react with the chromium carbide that fills the cracks and the carbide-rich bonding layer, but not at higher temperatures. Thus, it has been found to be important that the temperatures be above 1600° F., preferably above 1700° F., more preferably above 1750° F., when the protective layers of this invention are contacted with steam.

In a further embodiment for forming a protective layer, the chromium layer is bonded to steel in the presence of a nitrogen-containing compound at elevated temperature. This has the advantage of forming not only a carbide-rich bonding layer, but also results in the filling of cracks in the chromium layer with chromium nitride which effectively seals off the carbide-rich bonding layer from $H_2O$/steam attack. This coated steel is especially useful in preventing carburization and metal dusting, for example in steam/ ethylene crackers. Moreover, and unexpectedly, the coated and cured metal surface significantly and substantially reduces the formation of coke in ethylene cracker furnace tubes. Our experiments indicate that this coating is even better than quartz at minimizing coke formation.

It is preferable to perform this curing process in the absence of oxygen-containing compounds, such as air, elemental oxygen, and steam.

When forming the protective chromium layer in the presence of a nitrogen-containing compound, curing in elemental nitrogen ($N_2$) is preferred. However, curing in other gases containing compounds having nitrogen atoms, such as ammonia or organic amines, can also be performed.

Heat treating the chromium coated steel in the presence of a nitrogen-containing compound is performed at temperatures between 1400° and 2000° F., preferably between 1600° and 1900° F. More preferably, curing is performed at the temperature expected at the metal wall during hydrocarbon cracking. The resulting coated steel is believed to comprise a metallic chromium protective layer, a chromium carbide bonding layer, and chromium nitride-filled cracks and voids.

It is preferable to perform heat treatment in the presence of a nitrogen-containing compound before contacting the coated metal surface with hydrocarbons, especially hydrocarbons and steam, or hydrocarbons, steam and sulfur. It is also preferable to maintain the protective layer-coated steel at temperatures near the cracking temperature after heat treatment so that additional cracks are not produced.

It has been observed that the high operating temperatures used in steam cracking (1750°–1850° F.) stabilize chromium carbides and nitrides relative to chromium oxides. Conversely, at temperatures lower than about 1600° F., chromium oxides are stabilized relative to chromium carbides and nitrides. Therefore, it is preferable to maintain the protective layer-coated steel at high temperatures so that chromium oxides will not replace chromium carbides and nitrides, and the carbide-rich bonding layer will remain protected from steam attack over time. It is further preferred that the protective layer-coated steel is brought to high temperatures before adding steam, or that steam addition is minimized during the curing process.

Essentially any steel can be protected according to the invention including stainless steels. Chromium platings are preferably applied to heat-resistant nickel-rich steels for better long term stability. Nickel-rich steels have 18–40% Ni and 20–30% Cr. Examples of such steels include HP-50 (35% Ni, 26% Cr) and HK-40 (20% Ni, 20% Cr) steels. "Heat resistant" steels are useful because of their high temperature creep resistance.

For long term use at high temperatures, a steel should be chosen that inhibits diffusion of chromium from the protective layer into the steel, since significant diffusion of chromium into the steel could ultimately result in total consumption of the chromium protective layer. In this regard, it is preferable to use high chromium, high nickel steels, such as HP-50 and HK-40 steel.

The nitrogen-curing procedure is also effective for a tungsten and/or molybdenum protective layer. Mixtures of those metals with chromium can also be used. However, decoking procedures would have to be done carefully to avoid formation of W(+6) or Mo(+6) oxides, which are volatile at temperatures above about 1200° F. Preferred decoking procedures for tungsten and molybdenum protective coatings include oxidation temperatures of below 1000° F., more preferably below 900° F., and limiting the oxygen concentration below about 20%, more preferably below about 5%.

According to a thermal cracking operation of the present invention, a diluent fluid such as steam can be combined with a hydrocarbon feed such as ethane and/or propane and/or naphtha, and introduced into a cracking furnace. Within the furnace, the feed stream which has been combined with the diluent fluid will be converted to a gaseous mixture which primarily contains hydrogen, methane, ethylene, propylene, butadiene, and small amounts of heavier gases. At the furnace exit this mixture will be cooled to remove most of the heavier gases, and then compressed. The compressed mixture can then be routed through various distillation columns where the individual components such as ethylene are purified and separated.

The cracking furnace may be operated at any suitable temperature or pressure. For example, in the process of steam cracking of light hydrocarbons to ethylene, the temperature of the fluid flowing through the cracking tubes increases during processing and will attain a temperature of about 1575° F. The wall temperatures of the cracking tubes will be even higher. Furnace temperatures of nearly 2100° F. may be reached. Typical pressures for a cracking operation will generally be in the range of about 5 to about 20 psig at the outlet of the cracking tube.

One advantage of the present process is that it can be operated with less steam. Steam is traditionally added to olefin crackers. In part it is added to passivate the coking and carburization tendency of the steel. At lower steam levels, the steel becomes carburized and embrittled relatively rapidly, leading to premature failure. Using the current invention, less steam can be used, for example, to increase throughput.

In order to determine whether carburization has occurred, a simple burn test can be used to differentiate between thermal coke and coke produced via metal dusting or iron containing materials. According to the test, a sample of coke is heated at 1500° F. in air. Metallic coke burns brick red under these conditions, while thermal coke does not.

To obtain a more complete understanding of the present disclosure, the following example illustrating certain aspects of the invention is set forth. It should be understood, however, that the disclosure is not limited in any way to the specific details set forth therein.

EXAMPLE 1

Chromium-plated steels were tested for their carburization and catalytic coking resistance in high temperature environments (e.g., 800° F.–2000° F.). In a cracking environment of 2000° F. for 1 hour in a carburizing gas of 7% $C_3H_8$ in $H_2$ bubbled through $H_2O$ doped with sufficient $CS_2$ to provide approximately 100 ppm sulfur, a chromium plated 304 stainless steel sample did not exhibit coking or carburization, whereas an untreated sample of INCOLOY 800, and samples of stannided and antimonided nickel-plated INCOLOY 800 did exhibit coking. In the complete absence of sulfur, the chromium-plated sample did exhibit coking, but much less than the untreated sample.

In the aforementioned test, chromium was applied as a plating and heat treated to weld or glue the chromium to the steel. The chromium plate was found to have reacted with the steel substrate to form a glue composed of CrFe and chromium carbide; with a coating of $Cr_2O_3$ forming on the exterior.

EXAMPLE 2

One environment which is particularly harsh is a halogen containing environment. The presence of halogens adversely affects raw steels. The chromium protective layers of the invention are surprisingly effective for isolating the steels from those halogen effects at high temperatures. The protective layers of the invention are effective at even high halogen concentrations.

The following tests were run to demonstrate the effectiveness of chromium protective layers for isolating underlying metallurgy from halogen containing environments. The tests were done in a Lindberg quartz tube furnace.

Samples of stainless steel, provided with stannide protective layers and chromium protective layers, were tested at 1000° F. and 1200° F. for twenty-one hours, in the presence of methylchloride. The coupons were placed in an open quartz boat within the hot zone of a tube furnace. The tube was flushed with nitrogen for a few minutes. Then the samples were exposed to a hydrocarbon gas. For experiments using 10,000 ppm halogen the gas was 1% $CH_3Cl$ in hydrogen. For those using 1,000 ppm halogen the gas was a mixture of 0.1% $CH_3Cl$ and 7% propane in hydrogen. Gas flows were 25 to 30 cc/min. at atmospheric pressure. The samples were rapidly brought to operating temperatures. The test results are shown in the following Table. A "pass" result means the samples did not substantially form coke on the metal surface.

TABLE

Effect of Chloride

| Ex. No. | Amount of MeCl, ppm | Temp. °F. | Raw Steel | Stannide Protective Layer | Chromium-Protective Layer |
|---|---|---|---|---|---|
| 1 | 10,000 | 1000 | Fail | Pass | Pass |
| 2 | 10,000 | 1200 | Fail | Fail | Pass |
| 3 | 1,000 | 1200 | Fail | Pass | Pass |

The results show that both chromium and stannide protected steel can withstand high halogen concentrations at 1000° F., but the stannided protective layer is not as effective at 1200° F. Chromium protective layers were effective under all conditions tested.

EXAMPLE 3

Dry carburization tests were run using 7% $C_3H_8$ in $H_2$ over HP-50 steel chips in a Lindberg Quartz tube furnace. The results were:

|  | Cr "Paint"* on HP50 | Cr Plate** on HP50 | Untreated HP50 |
| --- | --- | --- | --- |
| 1600° F. | Trace of coke | Essentially coke free | Coked |
| 4 Hrs | Uncarburized | Uncarburized | Carburized |
| 2000° F. | Trace of coke | Substantially coke free | Coked |
| 2 Hrs | Uncarburized | Uncarburized | Carburized |

*$CrCl_2$ powder on HP-50 reduced 2 hrs. at 1500° F. in $H_2$
**Commercial hard Cr plate on HP-50 heat treated in $H_2$ at 1500° F. for 2 hrs.

Microscopy analysis revealed a chromium-carbide bonding layer between the chromium coatings and the underlying steel in the chromiumtreated samples. The untreated HP-50 showed deep and intense carburization.

EXAMPLE 4

Wet coking and carburization tests were run using 7% $C_3H_8$ in $H_2$ bubbled through water in a Lindberg Quartz tube furnace. The tests were done over Cr-plated steel. The results were:

|  | Cr Plate on HP50 | Untreated HP50 |
| --- | --- | --- |
| 1600° F. | Coke free | Coked |
| 4 Hrs | Uncarburized | Lightly carburized |
| 2000° F. | Essentially coke free | Coked |
| 2 Hrs | Uncarburized | Lightly carburized |

This example shows that, compared to Example 3, steam inhibits carburization. Microscopic analysis of the chromium-treated steel after the tests revealed a chromium-carbide bonding layer between the chromium coating and the underlying steel in the chromium-treated sample. This layer was thicker in the higher temperature experiment. Some chromium oxide was observed on the exterior surface and within the natural cracks of the chromium plate.

EXAMPLE 5

An HP-50 steel chip was treated with $CrCl_2$ powder and cured in pure $H_2$ at 1500° F. for 1 hour. Microscopy analysis revealed that the chip had a high quality, continuous, uniformly thick, and firmly and cleanly attached coating of chromium, 1 mil in thickness.

EXAMPLE 6

Two INCOLOY 800 steel chips were placed in a quartz sample boat. The first had been treated with a mixture of about equal amounts of $CrCl_2$ and $MoCl_5$ powders. The second chip (downstream from the first) had been treated with a mixture of $CrCl_2$ and $WCl_6$ powders. Pure $H_2$ gas was passed over the samples in a Lindberg quartz tube furnace at 1200° F. for two hours. Microscopy analysis revealed that the first chip had a metallic coating 1–2 microns thick of chromium with about 7% Mo. The second chip had received a 1 micron coating of chromium with about 20% W and 10% Mo.

This experiment demonstrates that mixed metal coatings can be prepared from mixtures of metal salts. The molybdenum and tungsten chlorides are volatile; nonetheless, the molybdenum and tungsten were incorporated into the metallic coating.

EXAMPLE 7

An HP-50 steel chip was coated with a mixture of finely ground $CrCl_3$ crystals in just enough petroleum jelly to make a viscous paint. The coated chip was cured in $H_2$ at 1500° F. for 1 hour. Microscopy analysis of a cross-section revealed a uniform coating of chromium :metal, tightly interlocked with a similarly thick, carbide-rich bonding layer onto the underlying steel.

EXAMPLE 8

Sample chips of chromium-plated 9 Cr 1 Mo steel, 304 stainless steel, and HP-50 steel were placed in a quartz sample boat and treated in dry nitrogen for two hours at 1800° F. in a quartz tube furnace. Petrographic microscopy analysis revealed no evidence of peeling of the chromium plate from any of the steel samples and, in no case, was there significant diffusion of iron or nickel into the chromium protective layer. Moreover, distinctive carbide-rich bonding layers were observed in all of the samples.

For example, with the chromium-plated 9 Cr 1 Mo steel, a single carbide layer formed between the chromium plate and the underlying steel. Three layers formed between the chromium plate and the 304 stainless steel: chromium ferride on the steel itself, followed successively by an iron-rich carbide and a chromium-rich carbide. Two chromium-rich carbide layers formed on the chromium-plated HP-50 steel: an inner layer containing nickel, and a nearly nickel-free outer layer.

Under the conditions of this test, no significant diffusion of chromium from the protective layer into the HP-50 steel was observed. However, them was extensive diffusion of chromium from the protective layer into the underlying 9 Cr 1 Mo steel, and some chromium diffusion was detected from the protective layer into the type 304 stainless steel. While the chromium-coated HP-50 steel may be preferred for use at high temperatures due to the resistance of chromium migration from the protective layer into the steel, the chromium-coated 9 Cr 1 Mo steel and type 304 stainless steel may be used advantageously in lower temperature environments.

Chromium nitride also formed as a coating on the surface of the chromium metal in all samples, as well as filling and sealing cracks that formed upon heating the chromium plates. The crack-filling chromium nitride was found to persist after exposure to pure hydrogen for an additional two hours at 1800° F.

EXAMPLE 9

The nitrided sample chips of chromium plated HP-50 steel of Example 8 were tested for coking and carburization in the presence of water and sulfur. These tests were run in a Lindberg Quartz tube furnace using 7% $C_3H_8$ in $H_2$. Sulfur (100 ppm) as $CS_2$ was added to the gas, which was then bubbled through water. The results were, that after 4 hours at 1800° F., the nitrided chromium plated HP-50 was essentially coke free. In contrast, the untreated HP-50 was coked.

EXAMPLE 10

A spreadable and flowable chromium paint was prepared. One part by weight of crystalline $CrCl_3$ and one part by weight of metallic chromium powder (1–5 microns, purchased from AEE [Atlantic Equipment Engineers, New Jersey]) were combined and ground using mortar and pestle to reduce the size of the $CrCl_3$ crystals. This mixture was then combined with 1 part by weight of 8% chromium Hex-Cem (chromium hexanoate [8% chromium] sold by Mooney Chemical [now OMG, Cleveland, Ohio]) and then diluted with about one part hexane. The hexane was gradually added until the mixture's viscosity was point-like. The resulting paint was applied to steel coupons (e.g., HK40 and HP50) using a paint brush. The coupons had been previously sanded and washed in acetone to remove oils. A second paint coating was sometimes applied after the first coating had dried, if the dried paint was less than 2 mils thick. Thereafter, the coupons were dried in air for 16 hours at room temperature.

The coated coupons were cured at 1400° F. in a pure hydrogen atmosphere for 48 hours. The conditions used for reduction included holding at 200° F. for one hour, then heating at 200° F./hr to 1100° F.; holding for 48 hours and then cooling to 200° F. Thereafter the coupons were held at 200° F. for approximately 10 hours and then cooled to room temperature. After cooling, the coupons appeared dark gray with a green tint in color, and were observed to have a uniform coating of chromium.

While the invention has been described above in terms of preferred embodiments, it is to be understood that variations and modifications may be used as will be appreciated by those skilled in the art. Essentially, therefore, there are many variations and modifications to the above preferred embodiments which will be readily evident to those skilled in the art and which are to be considered within the scope of the invention as defined by the following claims.

What is claimed is:

1. A process for cracking hydrocarbons comprising:
   (i) providing a carburization, abrasion and peeling resistant and coking resistant Group VIB metal protective layer to a steel portion of a cracking reactor system by (a) applying to the steel portion a Group VIB metal plating, cladding or other coating of Group VIB metal to a thickness effective to isolate the steel portion from hydrocarbons during operation, and (b) forming the protective layer, anchored to the steel portion through an intermediate carbide-rich bonding layer by curing the plating, cladding, or other coating in the presence of a nitrogen-containing compound for a time and at a temperature effective to form the intermediate carbide-rich bonding layer and to incorporate nitride material in a crack or cracks of the cured plating, cladding or other coating; and
   (ii) cracking hydrocarbon feed.

* * * * *